United States Patent
Penzes et al.

(10) Patent No.: US 8,703,468 B2
(45) Date of Patent: Apr. 22, 2014

(54) PORCINE CIRCOVIRUS TYPE 2B ISOLATE AND USES THEREOF

(75) Inventors: Zoltan Penzes, Budapest (HU); Ferenc Misák, Pilisborosjeno (HU); Tamás Tuboly, Budapest (HU); Attila Csagola, Baj (HU)

(73) Assignee: Ceva Sante Animale, Libourne, Cedex (FR)

( * ) Notice: Subject to any disclaimer, the term of this patent is extended or adjusted under 35 U.S.C. 154(b) by 0 days.

(21) Appl. No.: 13/142,090

(22) PCT Filed: Nov. 27, 2009

(86) PCT No.: PCT/EP2009/066007
§ 371 (c)(1),
(2), (4) Date: Nov. 2, 2011

(87) PCT Pub. No.: WO2010/061000
PCT Pub. Date: Jun. 3, 2010

(65) Prior Publication Data
US 2012/0040438 A1     Feb. 16, 2012

Related U.S. Application Data

(60) Provisional application No. 61/118,505, filed on Nov. 28, 2008.

(51) Int. Cl.
*C12N 7/00* (2006.01)
*C07K 14/005* (2006.01)
*A61K 39/00* (2006.01)

(52) U.S. Cl.
CPC ........ *C12N 7/00* (2013.01); *C12N 2750/00021* (2013.01); *A61K 2039/5254* (2013.01)
USPC .............................. 435/235.1; 435/5; 424/204

(58) Field of Classification Search
USPC ........................................................ 435/235
See application file for complete search history.

(56) References Cited

FOREIGN PATENT DOCUMENTS

WO    WO 99/29717      6/1999
WO    WO 2008/140414   11/2008

OTHER PUBLICATIONS

Boisseson et al., Molecular characterization of Porcine circovirus type 2 isolates from post-weaning multisystemic wastin syndrome-affected and non-affected pigs, 2004, Journal of General Virology, 85: pp. 293-304.*
Blanchard et al., Protection of swine against post-weaning multisystemic wasting syndrom (PMWS) by porcine circovirus type 2 (PCV2) proteins, 2003, Vaccine, 21: pp. 4565-4575.*
De Boisseson, C. et al. "Molecular characterization of *Porcine circovirus* type 2 isolates from post-weaning multisystemic wasting syndrome-affected and non-affected pigs" *Journal of General Virology*, 2004, pp. 293-304, vol. 85.
Misinzo, G. et al. "Inhibition of Endosome-Lysosome System Acidification Enhances Porcine Circovirus 2 Infection of Porcine Epithelial Cells" *Journal of Virology*, Feb. 2008, pp. 1128-1135, vol. 82, No. 3.
Roca, M. et al. "In vitro and in vivo characterization of an infectious clone of a European strain of porcine circovirus type 2" *Journal of General Virology*, 2004, pp. 1259-1266, vol. 85.
Database EMBL EMBO; Accession No. AY321993, "Porcine circovirus 2 strain Fh16", Jul. 15, 2003, pp. 1-2.
Database EMBL EMBO; Accession No. AAX83756, "Porcine circovirus type II B9 nucleotide sequence fragment #1", Aug. 27, 1999, p. 1.
Written Opinion in International Application No. PCT/EP2009/066007, Mar. 15, 2010, pp. 1-7.

* cited by examiner

*Primary Examiner* — Stacy B. Chen
*Assistant Examiner* — Barry A Chestnut
(74) *Attorney, Agent, or Firm* — Saliwanchik, Lloyd & Eisenschenk

(57) ABSTRACT

The present invention relates to the novel Porcine Circovirus type 2 subtype B (PCV2B-Rm) isolate which comprises a short duplication of sequence and is adapted to grow in cell culture and may be propagated at high titres constantly up to $10^6$ TCID$_{50}$ viral particles per mL. This novel isolate is particularly useful for the production of porcine circovirus type 2 (PCV2) vaccines, for treating and/or preventing and/or diagnosing porcine circovirus associated diseases, as well as for diagnosing the presence of porcine circovirus in pigs. The present invention also relates to novel cell clones derived from Swine Testicles (ST) useful for propagating PCV2 and to a method for production of PCV2 virus with particularly high titers.

7 Claims, 7 Drawing Sheets

FIGURE 2: SEQ ID NO: 1

```
ACCAGGCGCACTTCGGCAGCGGCAGCACTCGGCAGCAGCACCTCAGCAGCAACATGCCCAGCAAGAAGAATGGAAGAAGC
GGACCCCAACCCCATAAAAGGTGGGTGTTCACTCTGAATAATCCTTCCGAAGACGAGCGCAAGAAAATACGGATCTTCCAATATCCC
TATTTGATTATTTATTGTTGGCGAGGAGGGTAATGAGGAAGGACGAACACCTCACCTCCAGGGGTTCGCTAATTTTGTGAAGAAGCA
GACTTTTAATAAAGTGAAGTGGTATTTGGGTGCCCGCTGCCACATCGAGAAGAGCGAAAGGAACAGATCAGCAGAATAAAGAATACTGC
AGTAAAGAAGGCAACTTACTGCCGGTGTCTGGTGAGCTCCTAGATCTCGGAGCTGTGTGCAGAGCAGCACCCTGTAACGTTTGTCAGAAATT
TGGAGAGCGGGAAAATGCCGGAGTCTGGTGACCGTTGCAGAGACAGCACCCTGTAACGTTTGTCAGAAATTTCCGCGGGCTGGCTGTAAAGCAAATGGCTGCT
GAGCGGGAAAATGCAGAAGCGTGATTGAAGATAACACCACTAGAAACAAGTGGTGGGATGGTTACCATGGTGAAGAAGTGGTTGTTATTG
AATTTGCAGACCCGGAAACCACATACGTGCCCTGGATGATCTACTGAGACTGTGTGATAGATATCGAAATGGAATGGTACTCCTCCAGCTGTAGAAGCT
ATGACTTTTATGCTGGCTGCCTGGATGATCTACTGAGACTGTGTGATAGATATCGAAATGGAATGGTACTCCTCCAGCTGTAGAAGCT
ACCTTTTTGCCCGCAGTATTCTGATTCTGGTATTTGGAAGAATGCTACAGAACAATCACTTCGTTGAACAATCACTTCGATATTGTATTCCTGTCGTATATGTCTGTTTCGAACG
CTTTATCGGAGGATTACTTCCTTGGTATTTGGAAGAATGCTACAGAACAATCACTTCGATATTGTATTCCTGTCGTATATGTCTGTTTCGAACG
CCCCATGCCCTGAATTTCTGTTCGAAATAAAATTCTGTACATTGTACAGATTGTAGTCTCAGCCACGCTGATTTCTTTTGTTTGGTTGGAAGTAATC
GGGGGTCTTTAAGATGAATCTAGGACAGGTTTTGGGGGTAAAGTAGCGGGAGTGGTTATGCGGGAGGAGGAGTAGTTTT
CAATGCCGAGGCTACGTGTCGTCCGGATTTATTGCTCCACACCACTGAGAATAACAGAGAATAACAGACACTCGAGCCCACTCCCCTGTCACCCT
AATAGTGGAATCTAGGACAGGTTCATTAATATTGAATCTCATCATGTCCACCGCCCAGGAGGGCGTTTGACGTGGTTCGCTTGATAGTATAT
ACATAGGGTCATAGGTCGAGGCCAGGCCAGAATTCAACCTTAACCTTCTATTCTGTAGTATTCGTAGTATTCGTAGTATTCGAAGGCACACACAGGGCACAGAGGCACAGAGGGTTGAGCCCCC
GGGTGATCGGGGAGCAGGCCAGAATTCAACCTTAACCTTCTATTCTGTAGTATTCGTAGTATTCGTAGTATTCGAAGGCACACACAGGGCACAGAGGCACAGAGGGTTGAGCCCCC
TCCTGGGGAAGAAAGTCATTAATATTGAATCTCATCATGTCCACCGCCCAGGAGGGCGTTTGACGTGGTTCGCTTGATAGTATAT
CCGAAGGTGCGGGAGAGCGGGTGTTGAAGATGCCATTTTCCTTCCTTCTCCGTAACGCGTGGCGCTGACGAGCCAGGCGGCC
GGCGGGGATCGGCCAAGATGGCCTGGGGGCGGTGTCTTCTTCTCCGGTAACGCGTGGCGCTGACGAGCCAGGCGGCC
AAGTGCGCTGTAAGTATT
```

FIGURE 3: SEQ ID NO: 2

ACCAGCGGCACTTCGGCAGCGGCAGCACCTCGGCAGCACCTCAGCAGCAACATG

FIGURE 4: SEQ ID NO: 3

CGGCAGCACCT

```
PCV2A    1   MTYPRRRYRRRHRPRSHLGQILRRRPWLVHPRHRYRWRRKNGIFNTRLSRTFGYTVKRT
PCV2BRm  1   MTYPRRRYRRRHRPRSHLGQILRRRPWLVHPRHRYRWRRKNGIFNTRLSRTFGYTIKRT
             ********************************************************

PCV2A    61  TVTTPSWAVDMRFKIDDFVPPGGGTNKISIPFEYYRIRKVKVEFWPCSPITQDRGVGS
PCV2BRm  61  TVKTPSWAVDMRFNINDFLPPGGGSNPRSVPFEYYRIRKVKVEFWPCSPITQDRGVGS
             ** *********  ** ****   *  ******************************

PCV2A    121 TAVILDDNFVTKATALTYDPYVNYSSRHTIPQPFSYHSRYFTPKPVLDSTIDYFQPNNKR
PCV2BRm  121 SAVILDDNFVTKATALTYDPYVNYSSRHTITQPFSYHSRYFTPKPVLDSTIDYFQPNNKR
             * **************************** ******************************

PCV2A    181 NQLWLRLQTSGNVDHVGLGAAFENSKYDQDYNIRVTMYVQFREFNLKDPPLKP
PCV2BRm  181 NQLWLRLQTAGNVDHVGLGTAFENSIYDQEYNIRVTMYVQFREFNLKDPPLNP
             ********* ********* ***** *** *****************   *
```

PORCINE CIRCOVIRUS TYPE 2B ISOLATE AND USES THEREOF

CROSS-REFERENCE TO RELATED APPLICATIONS

This application is the U.S. national stage application of International Patent Application No. PCT/EP2009/066007, filed Nov. 27, 2009, which claims the benefit of U.S. Provisional Patent Application No. 61/118,505, filed Nov. 28, 2008, the disclosures of which are hereby incorporated by reference in their entireties, including all figures, tables and amino acid or nucleic acid sequences.

FIELD OF THE INVENTION

The present invention relates to a novel Porcine Circovirus type 2 isolate derived from subtype B which may be produced at high titres. The novel isolate is useful for the efficient production of PCV2 vaccines. The invention also concerns a mutation in the large intergenic region for increasing the replication titres of PCV2, and novel cell lines adapted for propagating PCV2 at high titres. The invention further concerns a method for treating and/or preventing PCV2 associated diseases, pigs' vaccination and PCV2 vaccination or diagnostic kits.

BACKGROUND OF THE INVENTION

Porcine circovirus (PCV) was originally identified as a contaminant of porcine kidney cell cultures (PK15 ATCC CCL-33). The PCV virion has been characterized as being an icosahedral, non-enveloped virus with a single-stranded circular DNA of about 1.76 kb. PCV was classified in the genus Circovirus of the Circoviridae family, which consists of other animal circoviruses such as psittacine beak-feather disease virus, goose circovirus, canary circovirus, and pigeon circovirus. Two genotypes of PCV have been recognized. The PK15 cell-derived PCV has been considered to be nonpathogenic to pigs, and is designated PCV type 1 (PCV1). On the other hand PCV type 2 (PCV2) has been accepted as the major infectious agent involved in several pigs diseases. PCV2 associated diseases cause significant economic losses to swine producers worldwide. A review of PCV2 associated infections have been well described in the patent WO2007/076520 and include for example Postweaning Multisystemic Wasting Syndrome (PMWS), Porcine Dermatitis and Nephropathy Syndrome (PDNS), Porcine Respiratory Disease Complex (PRDC), reproductive disorders, granulomatous enteris, exsudative epidermitis, necrotizing lymphadenitis, and congenital tremors. Occurrences of PCV2 subtype A (PCV2A) and PCV2 subtype B (PCV2B) have been reported particularly in 2000 in West Europe and in Central Europe in 2003. More recently similar changes have been reported in 2008 in wild boars.

Currently developed PCV2 vaccines such as CIRCOVAC (Merial), INGELVAC CircoFLEX (Boehringer Ingelheim Vetmedica), SUVAXYN PCV2 (Fort Dodge), are based on inactivated PCV2A, or on the expression of ORF2 gene of PCV2A by a baculovirus vector. It is thus necessary to develop PCV2 vaccines that would be broadly effective against all PCV2 associated diseases. However, current PCV2 strains subtype A or B present several weaknesses. Particularly, PCV2 viruses can only be produced at low titres, generally less than $10^5$ $TCID_{50}$ viral particles per mL. Also, these viruses cannot be maintained in tissue cultures and permanently infected cell lines. The Applicant has discovered a novel PCV2 isolate belonging to subtype B which can address the issues of PCV2 vaccines as developed so far, such as high titre growth and maintenance of PCV2 in tissue culture.

SUMMARY

The first aspect of the invention thus provides a novel Porcine Circovirus type 2 subtype B (PCV2B) isolate. The novel PCV2B isolate is designated PCV2B-Rm, and is adapted to grow in cell culture at higher yields of replication.

The second aspect of the present invention provides PCV2 vaccines comprising an immunologically effective amount of PCV2 virus or PCV2 antigen and a method of producing PCV2 vaccines.

A third aspect of the invention provides a nucleotide sequence comprising a short duplication of sequence as that of PCV2 virus of the first aspect, vectors or cells containing such nucleotide sequence and method of increasing the yield of replication of PCV2 virus in cultured cell lines.

According to fourth aspect, the present invention relates to methods of treating and/or preventing PCV2 associated diseases, and methods of immunizing or vaccinating non human animal subjects, such as pigs, swine, piglet, against PCV2 infections comprising administering the PCV2 vaccines of the second aspect of the invention.

According to the fifth aspect of the present invention, it is provided a method of diagnosing the presence of PCV2 virus in pigs, reagents used therefor, as well as diagnostic kits and diagnostic tests.

The sixth aspect of the present invention provides novel cell lines derived from Swine Testicles (ST), herein designated ST1D and ST6B. These novel cell lines are useful for propagating the novel PCV2B isolate, as well as other PCV2 virus. This aspect also relates to a method of producing PCV2B-Rm at high titres.

BRIEF DESCRIPTION OF THE DRAWINGS

FIG. 2 is the DNA sequence of the novel PCV2B-Rm (SEQ ID NO: 1).

FIG. 3 is the DNA sequence of the large intergenic region mutant (SEQ ID NO: 2).

Figure 4:
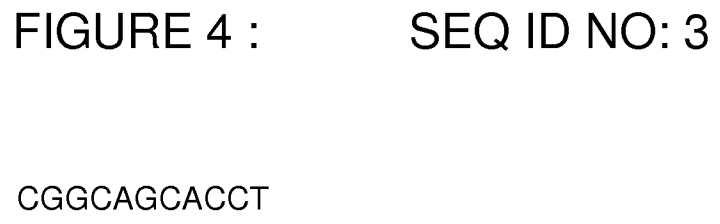

FIG. 4 shows the short duplicated nucleotide sequence (SEQ ID NO: 3) as inserted within the large intergenic region.

FIG. 5 is a partial schematic representation of the nucleotide sequence at positions 1743 to 64 of the genome of the novel PCV2-Rm. The sequence duplication comprising an additional H3 and Y2 sequence is circled underneath "Sequence duplication".

FIG. 6 shows the amino acid sequence comparison of the capsid protein sequence encoded by the ORF2 gene product for PCV2A and for PCV2B-Rm virus subtypes. Amino acid residues that differ between the two subtypes are shown in bold. Antigenic sites are boxed. Also, the underlined amino acid sequence is known to be toxic for cells and is thus usually removed before cloning and expression of the ORF2 gene in cells.

DETAILED DESCRIPTION OF THE INVENTION

Figure 1:
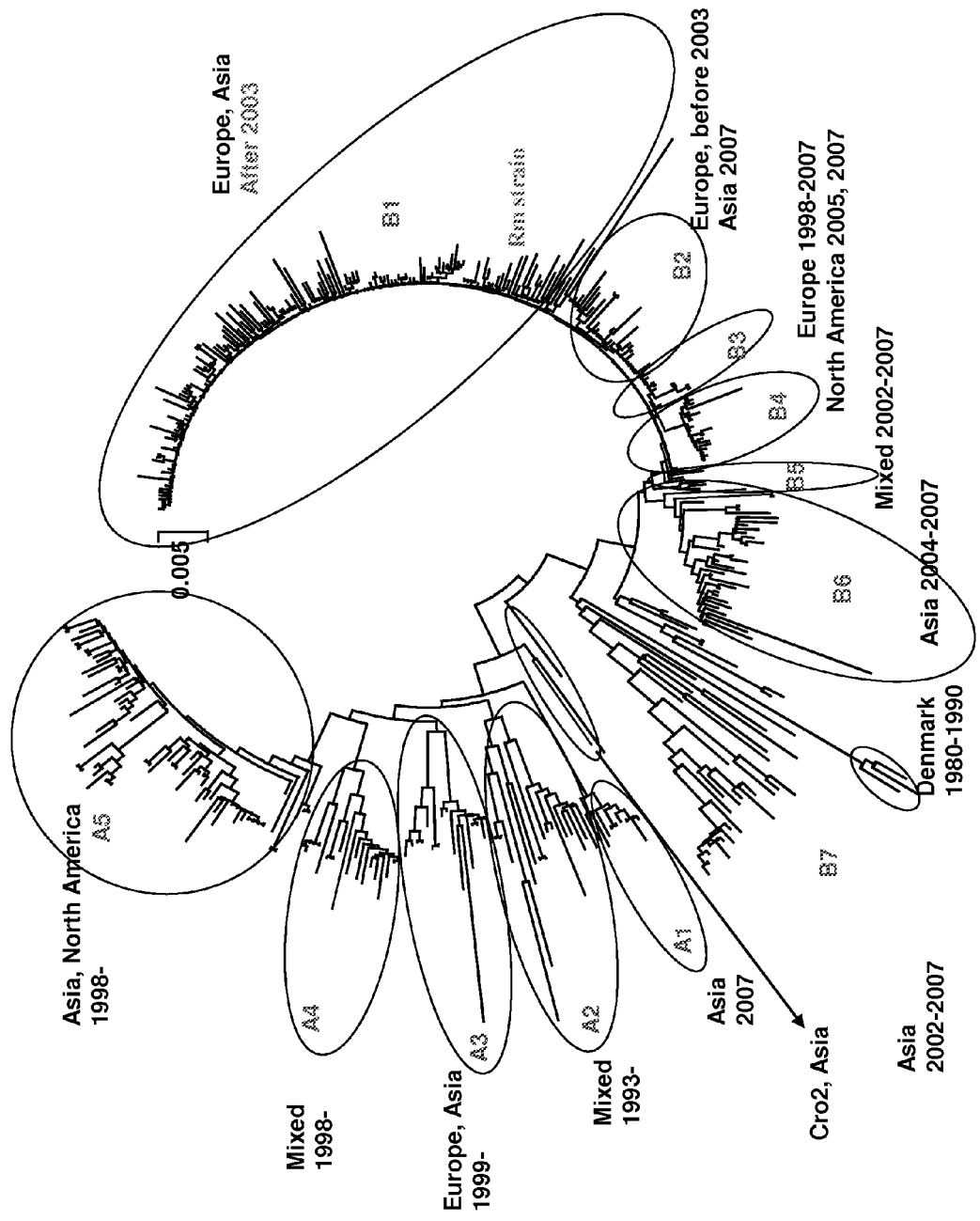
FIG. 1 is a phylogenic tree based on a complete genome analysis of known PCV2 subtypes A and B sequences in Europe, Asia, and America as of 2007. Position of the novel PCV2B-Rm virus is also provided.
Figure 7:
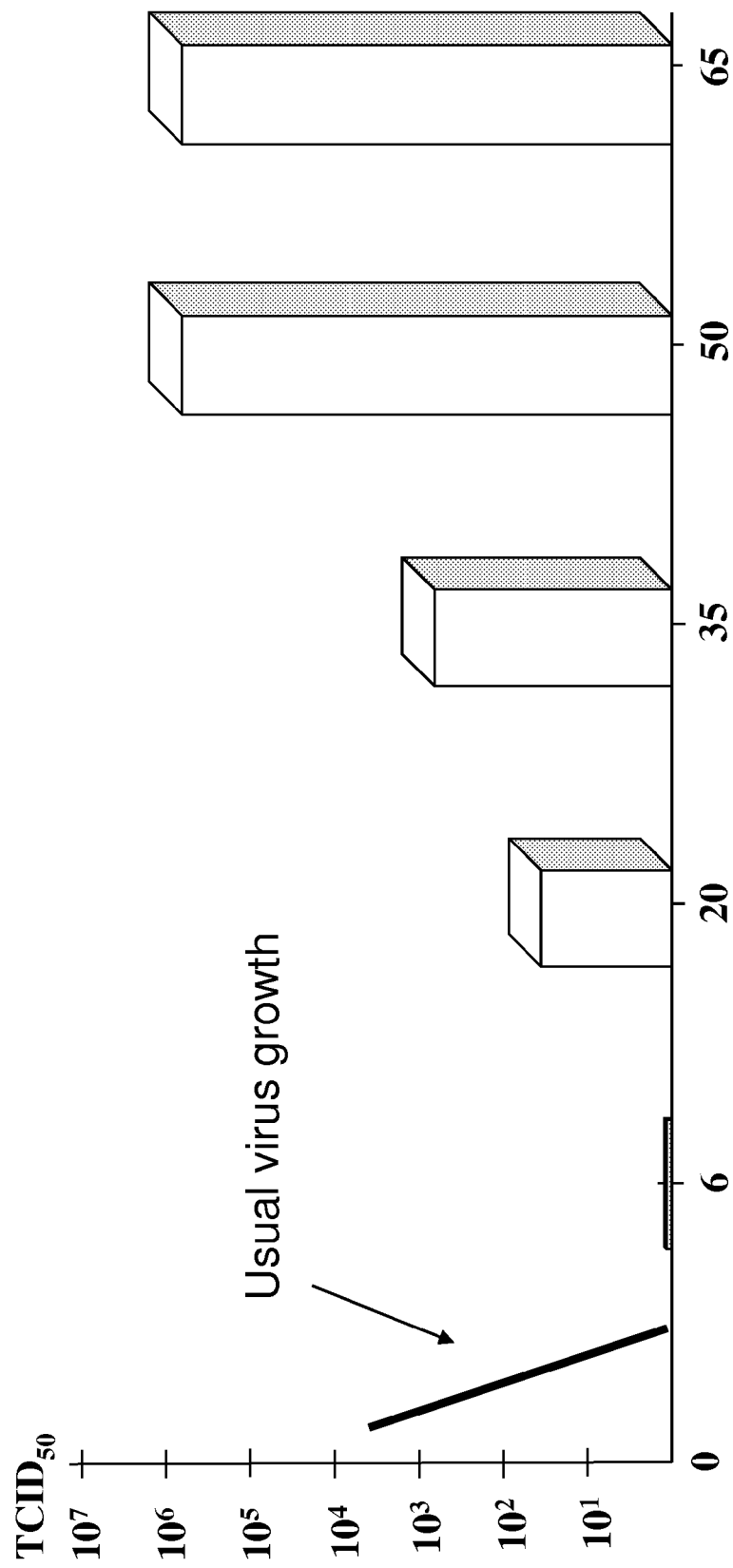
FIG. 7 is a graph showing usual virus growth and in parallel PCV2B-Rm growth in established ST cell lines according to the invention and yields of production at passages 6, 20, 35, 50 and 65.

The term "PCV2 vaccine" as used herein includes an agent which may be used to stimulate the immune system of pigs against PCV2 virus.

The term "immunization" includes the process of delivering an immunogen to a subject. Immunization may, for example, enable a continuing high level of antibody and/or cellular response in which T-lymphocytes can kill or suppress the pathogen in the immunized non-human animal, such as pig, which is directed against a pathogen or antigen to which the animal has been previously exposed.

According to a first aspect, the present invention thus relates to a novel Porcine Circovirus type 2 subtype B (PCV2B) isolate deposited at the Collection Nationale de Cultures de Microorganismes ("CNCM", Institut Pasteur, 25 rue de Docteur Roux, 75724 Paris Cedex 15, France) under the Budapest Treaty, on Nov. 27, 2008, and has accession number CNCM I-4094. The novel PCV2B isolate is designated PCV2B-Rm. PCV2B-Rm is adapted to grow in cell culture and is capable of being produced with higher titres as compared to wild-type PCV2 virus. The novel PCV2B-Rm may be produced at high titres constantly up to $10^6$ TCID$_{50}$ viral particles per mL, from $10^5$ to $10^6$ TCID$_{50}$ viral particles per mL, or more. Preferably, the PCV2B-Rm may be produced at higher titres up to $10^7$ TCID$_{50}$ and up to $10^8$ TCID$_{50}$ viral particles per mL. Most preferably, the PCV2B-Rm may be produced at titres from $10^5$ to $10^8$ TCID$_{50}$ viral particles per mL, or from $10^6$ to $10^8$ TCID$_{50}$ viral particles per mL, or from $10^7$ to $10^8$ TCID$_{50}$ viral particles per mL.

These increased yields of replication have been found to be attributable at least in part to the presence of a short duplication sequence in the large intergenic region of the genome of the PCV2 subtype B virus. Preferably, the duplication sequence comprises an 11 base pair duplication sequence as set forth in SEQ ID NO: 3 inserted in the large intergenic region.

The PCV2B-Rm of the invention are provided in an isolated form. The term "isolated" is meant to refer to PCV2B-Rm which is in other than a native environment of a wild-type virus. For example, the virus may be a component of a cell culture or other artificial medium where it can be propagated; as a component or a cell culture supernatant; as a component of a pharmaceutical composition; or partially or completely purified from its native environment.

This novel isolate may be produced in PK/15 cells or any other appropriate cell lines for example for their propagation, or for the production of antigens, either whole antigen, such as inactivated or attenuated virus, or subunits, such as parts of the virus, or immunogenic peptides thereof. PCV2B-Rm are preferably produced in novel adapted cell lines derived from Swine testicles (ST), designated ST1D and ST6B, which have been deposited at the Collection Nationale de Cultures de Microorganismes ("CNCM", Institut Pasteur, 25 rue de Docteur Roux, 75724 Paris Cedex 15, France) under the Budapest Treaty, on Nov. 27, 2008, and have accession No. CNCM I-4093 and CNCM I-4092, respectively.

According to a second aspect, the present invention relates to antigens or immunogens derived from the novel circovirus isolates and PCV2 vaccines, which induce a specific immune response in a host animal The PCV2 vaccine may comprise a whole PCV2-Rm, killed, inactivated, a subunit or a portion thereof, a recombinant vector containing an insert with immunogenic properties, a piece or fragment of DNA capable of inducing an immune response, a protein, a polypeptide, or a combination there. Such PCV2 vaccine compositions can be prepared according to standard techniques well known to those skilled in the art.

PCV2 vaccines may be based on novel circovirus isolate in the inactivated state. Methods of preparing inactivated viruses are well known in the art. Inactivation may be carried out by exposing the virus to a chemical agent such as formaldehyde, paraformaldehyde, β-propiolactone, ethyleneimine, binary ethyleneimine (BEI), thimerosal, or by derivatives thereof. Alternatively, inactivation may be carried out by physical treatments such as heat treatment or sonication. Methods of inactivation are well known to those of skill in the art. The inactivated pathogen may be concentrated by conventional concentration techniques, in particular by ultrafiltration, and/or purified by conventional purification means, in particular using chromatography techniques including but not limited to gel-filtration, ultracentrifugation on a sucrose gradient, or selective precipitations, in particular in PEG.

PCV2 vaccines of the invention comprise an immunologically effective amount of the circovirus or an immunogen as described above in a pharmaceutically acceptable vehicle. As a result of the vaccination with an immunologically effective amount of PCV2 vaccine, pigs become at least partially or completely immune to PCV2 infections, or resistant to developing moderate or severe PCV2 infections. PCV2 vaccines may be used to elicit a humoral and/or a cellular response.

PCV2 infections or associated diseases include inter alia Postweaning Multisystemic Wasting Syndrome (PMWS), Porcine Dermatitis and Nephropathy Syndrome (PDNS), Porcine Respiratory Disease Complex (PRDC), reproductive disorders, granulomatous enteris, exsudative epidermitis, necrotizing lymphadenitis, and congenital tremors. Preferably, a non-human animal subject, such as pig, is protected to an extent in which one to all of the adverse physiological symptoms or effects of PCV2 infections are significantly reduced, ameliorated or totally prevented.

The present invention also relates to the combination of PCV2 vaccine comprising a PCV2 subtypes A and B combination for treating PCV2 infections and associated diseases [Gupi P. S. Nayar et al. (Can. Vet. J, vol. 38, 1997: 385-387) and Clark E. G. (Proc. Am. Assoc. Swine Prac. 1997; 499-501)].

In practice, the exact amount required for an immunologically effective dose may vary from subject to subject depending on factors such as the age and general condition of the subject, the nature of the formulation and the mode of administration. Appropriate "effective amount" may be determined by one of ordinary skill in the art using only routine experimentation. For instance, methods are known in the art for determining or titrating suitable dosages of PCV2 vaccine to find minimal effective dosages based on the weight of the non human animal subject, concentration of the vaccine and other typical factors. The dosage of the vaccine, concentration of components therein and timing of administering the vaccine, which elicit a suitable immune response, can be determined by methods such as by antibody titrations of sera, e.g., by ELISA and/or seroneutralization assay analysis and/or by vaccination challenge evaluation.

PCV2 vaccines according to the present invention are particularly advantageous as they are formulated from PCV2B compositions which comprise from $10^5$ to $10^8$ TCID$_{50}$ viral particles per mL as described above.

PCV2 vaccines may comprise other ingredients, well known by one of ordinary skill in the art, such as pharmaceutically acceptable carriers, excipients, diluents, adjuvants, freeze drying stabilizers, wetting or emulsifying agents, pH buffering agents, gelling or viscosity enhancing additives, and preservatives, depending on the route of administration.

Examples of pharmaceutically acceptable carriers, excipients or diluents include, but are not limited to demineralised or distilled water; saline solution; vegetable based oils such as peanut oil, arachis oil, safflower oil, olive oil, cottonseed oil, maize oil, sesame oil, or coconut oil; silicone oils, including polysiloxanes, such as methyl polysiloxane, phenyl polysiloxane and methylphenyl polysolpoxane; volatile silicones; mineral oils such as light liquid paraffin oil, or heavy liquid paraffin oil; squalane; cellulose derivatives such as methyl cellulose, ethyl cellulose, carboxymethylcellulose, carboxymethylcellulose sodium salt, or hydroxypropyl methylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; carrageenan; gum tragacanth or gum acacia, and petroleum jelly. Typically, the carrier or carriers will form from 10% to 99.9% by weight of the vaccine composition and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Examples of adjuvants include, but are not limited to, aluminium hydroxide (alum), immunostimulating complexes, non-ionic block polymers or copolymers, cytokines (like IL-1, IL-2, IL-7, IFN-α, IFN-β, IFN-y, etc.), saponins, monophosphoryl lipid A (MLA), muramyl dipeptides (MDP) and the like. Other suitable adjuvants include, for example, aluminium potassium sulphate, heat-labile or heat-stable enterotoxin isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

Examples of freeze-drying stabilizer may be for example carbohydrates such as sorbitol, mannitol, starch, sucrose, dextran or glucose, proteins such as albumin or casein, and derivatives thereof.

PCV2 vaccines may additionally comprise at least one immunogen from at least one additional pathogen, e.g., a pig pathogen such as *Actinobacillus pleuropneunomia*; Adenovirus; Alphavirus such as Eastern equine encephalomyelitis viruses; *Balantidium coli; Bordetella bronchiseptica; Brachyspira* spp., preferably *B. hyodyentheriae, B. pilosicoli, B. innocens, Brucella suis*, preferably biovars 1, 2 and 3; Classical swine fever virus, African swine fever virus; Chlamydia and *Chlamydophila* sp. and preferably *C. pecorum* and *C. abortus; Clostridium* spp., preferably *Cl. difficile, Cl. perfringens* types A, B and C, *Cl. novyi, Cl. septicum, Cl. tetani*; Digestive and respiratory Coronavirus; *Cryptosporidium parvum; Eimeria* spp; *Eperythrozoonis suis* currently named *Mycoplasma haemosuis; Erysipelothrix rhusiopathiae; Escherichia coli; Haemophilus parasuis*, preferably subtypes 1, 7 and 14; Hemagglutinating encephalomyelitis virus; *Isospora suis*; Japanese Encephalitis virus; *Lawsonia intracellularis; Leptospira* spp., preferably *Leptospira australis, Leptospira canicola, Leptospira grippotyphosa, Leptospira icterohaemorrhagicae, Leptospira interrogans, Leptospira Pomona* and *Leptospira tarassovi; Mannheimia haemolytica; Mycobacterium* spp. preferably, *M. avium, M. intracellulare* and *M. bovis: Mycoplasma hyponeumoniae*; Parvovirus; *Pasteurella multocida*; Porcine cytomegolovirus; Porcine parovirus, Porcine reproductive and respiratory syndrome virus: Pseudorabies virus; Rotavirus; Sagiyama virus; *Salmonella* spp. preferably, *S. thyhimurium* and *S. choleraesuis; Staphylococcus* spp. preferably, *S. hyicus; Streptococcus* spp., preferably *Strep. suis*; Swine cytomegalovirus; Swine herpes virus; Swine influenza virus; Swine pox virus; *Toxoplasma gondii*; Vesicular stomatitis virus and virus of exanthema of swine; or other isolates and subtypes of porcine circovirus.

PCV2 vaccines may be liquid formulations such as an aqueous solution, water-in-oil or oil-in-water emulsion, syrup, an elixir, a tincture, a preparation for parenteral, subcutaneous, intradermal, intramuscular or intravenous administration (e.g., injectable administration), such as sterile suspensions or emulsions. Such formulations are known in the art and are typically prepared by dissolution of the antigen and other typical additives in the appropriate carrier or solvent systems. Liquid formulations also may include suspensions and emulsions that contain suspending or emulsifying agents. Preferred PCV2 vaccines comprise inactivated PCV2B-Rm according to the invention in the forms of emulsions, for example water-in-oil or oil-in-water, which may be prepared according to well-known techniques in the art.

The route of administration can be percutaneous, via mucosal administration, or via a parenteral route (intradermal, intramuscular, subcutaneous, intravenous, or intraperitoneal). Vaccines compositions according to the present invention may be administered alone, or can be co-administered or sequentially administered with other treatments or therapies. PCV2 vaccines as described above may preferably comprise the combination of PCV2 virus subtypes A and B, for vaccinating pigs against PCV2 infections or associated diseases.

According to a third aspect, the present invention relates to a nucleic acid molecule comprising full or partial sequences of the genome of the novel PCV2B-Rm. Particularly, the nucleic acid molecule comprises a nucleotide sequence as set forth in SEQ ID NO: 1, a fragment thereof, a nucleotide sequence having an homology of at least 99%, 99.1%, 99.2%, 99.3%, 99.4% 99.5%, 99.6%, 99.7%, 99.8%, or 99.9% with the nucleotide sequence as set forth in SEQ ID NO: 1, a nucleotide sequence which is capable of hybridizing to the nucleotide sequence as set forth in SEQ ID NO: 1, or to a sequence corresponding thereto within the degeneration of the genetic code under conditions of high stringency.

Preferably, the nucleic acid molecule may also comprise a nucleotide sequence corresponding to the modified large intergenic region as set forth in SEQ ID NO: 2, a fragment thereof, a nucleotide sequence having a homology of at least 80%, 85%, 90%, 92%, 95%, 97%, or 99% to the nucleotide sequence as set forth in SEQ ID NO: 2, a nucleotide sequence which is capable of hybridizing to the nucleotide sequence as set forth in SEQ ID NO: 2, or to a sequence corresponding thereto within the degeneration of the genetic code under conditions of high stringency.

Alternatively, the nucleic acid molecule according to the present invention may comprise an 11 base pair duplication sequence in the large intergenic region as set forth in SEQ ID NO: 3, a nucleotide sequence having a homology of at least 70%, 75%, 80%, 85%, 90%, 92%, 95%, 97%, or 99% to the nucleotide sequence as set forth in SEQ ID NO: 3, or a nucleotide sequence which is capable of hybridizing to the nucleotide sequence as set forth in SEQ ID NO: 3, or to a sequence corresponding thereto within the degeneration of the genetic code under conditions of high stringency.

According the invention, this nucleic acid molecule may comprise the genomic sequence of a wild type PCV2 virus wherein a duplication sequence is inserted in the large intergenic region. The duplication sequence as inserted within the PCV2 virus genome is as set forth in SEQ ID NO: 2, or a nucleotide sequence which is capable of hybridizing to the nucleotide sequence as set forth in SEQ ID NO: 3, or to a sequence corresponding thereto within the degeneration of the genetic code under conditions of high stringency. Such genomic sequence may be derived any PCV2 virus subtype A or subtype B.

Nucleic acid molecule includes DNA or RNA, double-stranded or single-stranded analogues of DNA and RNA, such as those containing modified backbones. Single-stranded DNA or RNA may be the coding strand, also known as the sense strand, or it may be the non-coding strand, also referred to as the anti-sense strand.

The degree of homology between two nucleic acid sequences may be determined by means of computer programs known in the art such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), Journal of Molecular Biology, 48, 443-453). Using GAP with the following settings for DNA sequence comparison: GAP creation penalty of 5.0 and GAP extension penalty of 0.3. Nucleic acid molecules may be aligned to each other using the Pileup alignment software, available as part of the GCG program package, using, for instance, the default settings of gap creation penalty of 5 and gap width penalty of 0.3.

Suitable experimental conditions for determining whether a given nucleic acid molecule hybridises to a specified nucleic acid may involve pre-soaking of a filter containing a relevant sample of the nucleic acid to be examined in 5×SSC for 10 minutes, and pre-hybridisation of the filter in a solution of 5×SSC, 5×Denhardt's solution, 0.5% SDS and 100 μg/ml of denatured sonicated salmon sperm DNA, followed by hybridisation in the same solution containing a concentration of 10 ng/ml of a P-dCTP-labeled probe for 12 hours at approximately 45° C., in accordance with the hybridisation methods as described in Sambrook et al. (1989; Molecular Cloning, A Laboratory Manual, 2nd edition, Cold Spring Harbour, N.Y.). The filter is then washed twice for 30 minutes in 2×SSC, 0.5% SDS at least 55° C. (low stringency), at least 60° C. (medium stringency), at least 65° C. (medium/high stringency), at least 70° C. (high stringency), or at least 75° C. (very high stringency). Hybridisation may be detected by exposure of the filter to an x-ray film.

Figure 5:
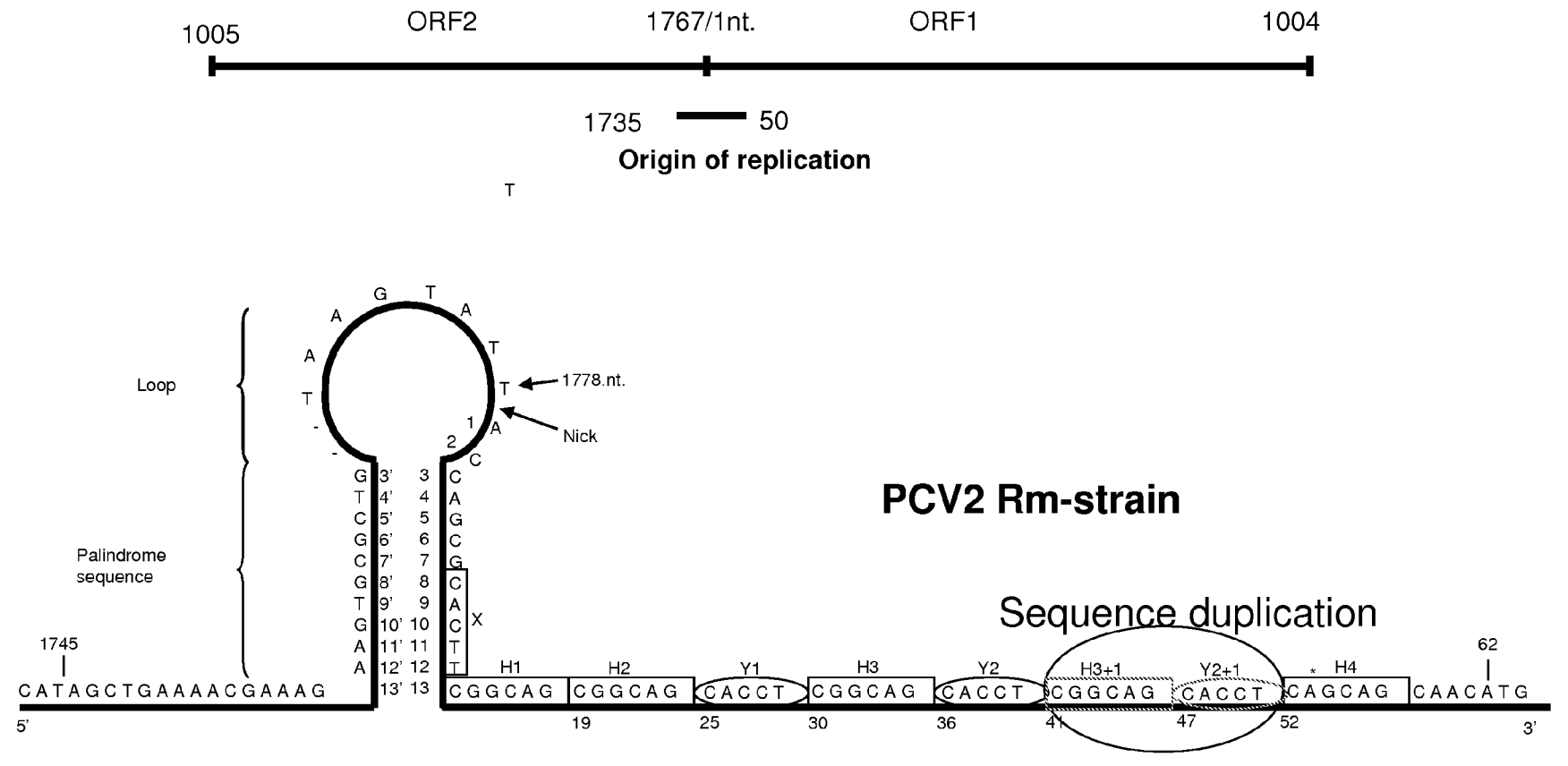

As described in the Examples below such engineered PCV2 virus may be produced by introducing a duplication sequence in the large intergenic sequence into the genome of a PCV2 clone. Preferably, the duplication sequence is an 11 bp sequence as set forth in SEQ ID NO: 3. Such duplication sequence may be inserted between nucleotides at positions 41 and 52 of the PCV2B genome as shown in FIG. 5. Methods for sequence insertions are well known in the art and can be readily accomplished by the skilled person. Genome of PCV2B and more particularly subtype B1, B2, B4, B5 or B6 may be modified according to the present invention. Preferably the duplication sequence is inserted in the genome of a PCV2 subtype B1 virus having 1767 bp (GenBank No. DQ233257) to generate the modified genome as in the above-described PCV2B-Rm having 1778 bp is displayed in FIG. 2 and SEQ ID NO: 1.

The nucleic acid molecules according to the invention may be provided in the form of a nucleic acid molecule per se such as naked nucleic acid molecules; a vector; virus or host cell etc, either from prokaryotic or eukaryotic origin. Vectors include expression vectors that contain a nucleic acid molecule of the invention. The vectors of the present invention may, for example, comprise a transcription promoter, and a transcription terminator, wherein the promoter is operably linked with the nucleic acid molecule, and wherein the nucleic acid molecule is operably linked with the transcription terminator.

In one embodiment there is provided a host cell transformed with a nucleic acid molecule according to the invention. Suitable examples of host cells will be known to those skilled in the art or can be readily selected by those skilled in the art. Host cells may, for example, include eukaryotic and prokaryotic cells. Examples of eukaryotic cells include mammalian (e.g., pig), fungal (e.g. *Saccharomyces cerevisiae*), insect and plant cells. Prokaryotic cells include, for example, *E. coli*.

PCV2 vaccine according to the invention may thus be provided in the form of whole PCV2B-Rm virus or in other forms, e.g., as nucleic acid molecules or vectors carrying such nucleic acid molecules as described above. Such nucleic acid comprises an 11 base pair duplication sequence which results in an increase yield of replication of the virus as compared with wild type viruses.

According to fourth aspect, the present invention provides a method of immunizing or inducing immune response in pigs comprising administering PCV2 vaccines comprising high titre of PCV2B-Rm virus as described above as well as method of vaccination in pigs, and methods of treating and/or preventing PCV2 associated diseases.

As mentioned above, PCV2 infections or associated diseases include inter alia Postweaning Multisystemic Wasting Syndrome (PMWS), Porcine Dermatitis and Nephropathy Syndrome (PDNS), Porcine Respiratory Disease Complex (PRDC), reproductive disorders, granulomatous enteris, exsudative epidermitis, necrotizing lymphadenitis, and congenital tremors.

The method comprises administering a therapeutically effective dose of the PCV2 vaccine. The vaccines of the invention can conveniently be administered intranasally, transdermally (i.e., applied on or at the skin surface for systemic absorption), parenterally, ocularly, etc. The parenteral route of administration includes, but is not limited to, intramuscular, intravenous, intraperitoneal routes and the like.

The dosage of the PCV2 vaccine made according to the present invention will depend on the species, breed, age, size, vaccination history, health status of the animal to be vaccinated, as well as of the route of administration, i.e., subcutaneous, intradermal, oral intramuscular or intravenous administration.

The vaccines of the invention can be administered as single doses or in repeated doses. The vaccines of the invention can be administered alone, or can be administered simultaneously or sequentially administered with one or more further compositions, such as for example other porcine immunogenic or vaccine compositions. Where the compositions are administered at different times the administrations may be separate from one another or overlapping in time.

In one embodiment, the vaccine compositions containing the PCV2B-Rm of the invention are administered to a subject susceptible to or otherwise at risk for PCV2 infection to enhance the subject own immune response capabilities. The subject to which the vaccine is administered is in one embodiment a pig. However, the subject may be any animal (e.g., non human mammal) in which it may be desirable to elicit an immune response to the virus. The animal may be susceptible to infection by PCV2 or a closely related virus.

PCV2 vaccines of the invention are preferably administered to pigs, adult pigs, but also to young pigs, piglets or to pregnant females, or to other types of non human mammals. Vaccination of pregnant females is particularly advantageous as it confers passive immunity to the newborns via the transmission of maternal antibodies. The pigs may be less than 7, 6, 5, 4, 3, 2 or 1 week old; 1 to 6 weeks old; 2 to 5 weeks old; or 3 to 4 weeks old. For instance, "test" animals may be administered the PCV2 vaccine of the invention in order to evaluate the performance of the PCV2 vaccine with a view to eventual use or development of a vaccine for pigs. Desirably, the vaccine is administered to a subject who has not yet been exposed to the PCV2 virus. Preferably, the subject is a pig which is in need of vaccination against Postweaning Multisystemic Wasting Syndrome (PMWS) and/or Porcine Dermatitis and Nephropathy Syndrome (PDNS).

The present invention includes a combination vaccine, comprising PCV2 vaccines of the invention and at least one immunogenic active component effective against another disease-causing organism in swine such as for example *Actinobacillus pleuropneunomia*; Adenovirus; Alphavirus such as Eastern equine encephalomyelitis viruses; *Balantidium coli*; *Bordetella bronchiseptica*; *Brachyspira* spp., preferably *B. hyodyentheriae, B. pilosicoli, B. innocens, Brucella suis*, preferably biovars 1, 2 and 3; Classical swine fever virus, African swine fever virus; Chlamydia and *Chlamydophila* sp. and preferably *C. pecorum* and *C. abortus*; *Clostridium* spp., preferably *Cl. difficile, Cl. perfringens* types A, B and C, *Cl. novyi, Cl. septicum, Cl. tetani*; Digestive and respiratory Coronavirus; *Cryptosporidium parvum; Eimeria* spp; *Eperythrozoonis suis* currently named *Mycoplasma haemosuis; Erysipelothrix rhusiopathiae; Escherichia coli; Haemophilus parasuis*, preferably subtypes 1, 7 and 14; Hemagglutinating encephalomyelitis virus; *Isospora suis*; Japanese Encephalitis virus; *Lawsonia intracellularis; Leptospira* spp., preferably *Leptospira australis, Leptospira canicola, Leptospira grippotyphosa, Leptospira icterohaemorrhagicae, Leptospira interrogans, Leptospira Pomona* and *Leptospira tarassovi; Mannheimia haemolytica; Mycobacterium* spp. preferably, *M. avium, M. intracellulare* and *M. bovis: Mycoplasma hyponeumoniae*; Parvovirus; *Pasteurella multocida*; Porcine cytomegalovirus; Porcine parovirus, Porcine reproductive and respiratory syndrome virus: Pseudorabies virus; Rotavirus; Sagiyama virus; *Salmonella* spp. preferably, *S. thyhimurium* and *S. choleraesuis; Staphylococcus* spp. preferably, *S. hyicus; Streptococcus* spp., preferably *Strep. suis*; Swine cytomegalovirus; Swine herpes virus; Swine influenza virus; Swine pox virus; *Toxoplasma gondii*; Vesicular stomatitis virus and virus of exanthema of swine or other isolates and subtypes of porcine circovirus.

The present invention provides a container comprising an immunologically effective amount the PCV2 vaccine as described above. The invention also provides vaccination kits comprising an optionally sterile container comprising an immunologically effective amount of the PCV2 vaccine, means for administering the vaccine to pigs, and eventually an instruction manual including information for the administration of the immunologically effective amount the composition into pigs for treating and/or preventing PCV2 associated diseases.

The present invention further relates to a method of generating an antibody which is capable of binding to PCV2 virus or sub-units thereof. The method may comprise immunizing an animal, such as a rabbit, guinea pig, or rodent and harvesting the antibody produced thereby. The antibodies of the invention may be polyclonal or monoclonal antibody preparations, monospecific antisera, human antibodies, or may be hybrid or chimeric antibodies, such as humanized antibodies, altered antibodies (Fab')2 fragments, F(ab) fragments, Fc fragments, single-domain antibodies, dimeric or trimeric antibody fragments or constructs, or functional fragments thereof which bind to the antigen in question. Antibodies may be produced using techniques well known to those of skill in the art and disclosed in "A Laboratory Manual, Harlow and Lane, eds., Cold Spring Harbor Laboratory, N.Y. (1988)".

According to the fifth aspect, a method of diagnosing the presence of circovirus in pigs, reagents used therefor, and diagnostic kits are further provided in the present invention. Its subject is thus diagnostic tests and methods relating thereto using reagents.

Based on the nucleotide sequences as described above, it is possible to produce reagents capable of recognizing porcine circoviruses. A skilled person in the art would be able to select fragments of around 20 to 50 bp within SEQ ID NO: 1-3 in order to carry a specific diagnosis. Therefore, DNA sequences disclosed herein and their fragments may be used as probes and/or primers for detecting presence of circovirus by hybridization or PCR experiments. Antigens encoded by the virus or expressed via a vector may also be used as a reagent for diagnostic purpose may be detected by immunofluorescence or Western blotting experiments. Monoclonal or polyclonal antibodies as described above may be used in diagnostic tests and reagents according to techniques which are well known in the art, for example by ELISA and immunochromatography.

Diagnostic kit thus may comprise DNA probes or primers, antigens and/or polyclonal or monoclonal antibodies specific for PCV2 virus, and diagnostic testing may be performed on a sample of physiological fluid (blood, plasma, serum and the like) or a sample of tissue (ganglia, liver, lungs, kidneys and the like) obtained from a pig to be tested.

The invention also relates to a method of increasing yield of production of PCV2 virus comprises inserting within the intergenic region of the genome of PCV2 subtype B virus, a duplication sequence, such as the nucleotide sequence as set forth in SEQ ID NO: 3, a nucleotide sequence having a homology of at least 70%, 75%, 80%, 85%, 90%, 92%, 95%, 97%, or 99% to the nucleotide sequence as set forth in SEQ ID NO: 3, or a nucleotide sequence which is capable of hybridizing to the nucleotide sequence as set forth in SEQ ID NO: 3. As described above, the duplication sequence may be inserted in the large intergenic region of the PCV2 subtype B virus, including for example subtypes B1 to B6.

The present invention also relates to a method of producing PCV2 virus as well as a suitable host cell for production of the novel PCV2B-Rm. A wide variety of host cells may be useful for the production of the novel PCV2B-Rm and include porcine cells such as porcine kidney cells, e.g., PK15 cells which are well known in the art.

According to sixth aspect, the present invention relates to novel cell lines derived from Swine Testicles (ST) cells, which can be permanently infected so as to produce PCV2 virus with a very high titres constantly up to $10^6$ TCID$_{50}$ viral particles per mL or higher, up to $10^7$ TCID$_{50}$ or up to $10^8$ TCID$_{50}$ viral particles per mL. Two clones designated ST1D and ST6B have been deposited at the Collection Nationale de Cultures de Microorganismes ("CNCM", Institut Pasteur, 25 rue de Docteur Roux, 75724 Paris Cedex 15, France) under the Budapest Treaty, on Nov. 27, 2008, and have accession numbers CNCM I-4093 and CNCM I-4092, respectively. Novel ST cell lines are thus useful for obtaining high yields of PCV2 subtype B virus production. Novel ST cell lines are also useful for efficient methods of production of PCV2 subtype B virus wherein the immunologically effective dose of PCV2 subtype B virus are particularly high. In addition, these novel cell clones may be used for propagating other porcine circoviruses, such as PCV2 either of subtypes A or B, with higher titres than the pig kidney cell lines PK/15. Propagation of PCV2B-Rm or other porcine are described in Example 3.

Suitable growth conditions for the host cell will be known to those skilled in the art or can be readily determined by those skilled in the art and will include the selection of, inter alia, suitable nutrient conditions. In one embodiment, the culture medium comprises at least water, salts, nutrients, essential amino acids, vitamins and antibiotics, and may also include one or more growth factors.

The following is provided to illustrate embodiments of the invention and should not be viewed as limiting the scope of the invention.

EXAMPLES

Example 1

Isolation and Culture of the PCV2B-Rm Virus

Lymph node samples of Porcine Circovirus type 2 (PCV2) infected pigs with clinical signs and post mortem findings characteristic of post-weaning multisystemic wasting syndrome were collected and frozen at −20° C. Thawed tissues were homogenized with equal volumes of DMEM (Dulbecco's Modified Minimum Essential Medium, GIBCO), supplemented with streptomycin (100 µg/ml) and penicillin (100 IU/ml), by grinding in sterile mortar. The preparation was clarified by centrifugation in a microcentrifuge at 5000 g for 10 minutes, 100 µl of the supernatant was used for the inoculation of Porcine Circovirus (PCV) free swine testicle cells at 50% confluency using the described medium supplemented with 10% fetal bovine serum (Invitrogen). The infected cultures when reaching confluence were trypsinized and seeded at 500 000 cells/ml onto 25 cm$^2$ plastic cell culture flasks (Corning). $\frac{1}{10}^{th}$ of the trypsinized cell suspension was used for PCV2 genome detection by polymerase chain reaction (PCR). The inoculated and the un-inoculated cell cultures were maintained at +37° C. in a CO$_2$ incubator. The process was sequentially repeated and the virus growth monitored at each step by PCR or indirect immune fluorescence assay.

Example 2

Detection of PCV2 Antigens by Immuno-Fluorescence

PCV2 specific polyclonal sera were produced in adult pigs free of PCV2 and other viral infections including: porcine parvovirus, PRRS and classical swine fever. Three pigs were injected intramuscular with the live PCV2B-Rm virus twice with 2 weeks interval and monitored for the appearance of clinical signs. Blood samples were taken weekly and at the termination of the immunization, 7 weeks after the first injection, when the animals were euthanized. The presence of PCV2 specific antibodies were detected as follows. Sera were tested individually, diluted tenfold, starting with 1:10 in PBS supplemented with 0.5% bovine serum albumin. PCV2 infected cells were fixed in an acetone/ethanol bath for 10 minutes at room temperature, and incubated for 1 hour at +37° C. with the serum dilutions. The secondary antibody was 1:100 diluted anti-pig IgG labeled fluorescein isothiocyanate, for one hour at +37° C. Excess antibodies were removed by rinsing in PBS after each step, and the reaction was observed in a fluorescent microscope under ultraviolet light.

Example 3

Routine Infection Protocol of ST1 D cells with PCV2B-Rm Virus 500.000 ST1D cells were seeded in a T25 flask (20,000 cells/cm$^2$) in 10 ml MEM-E medium supplemented with 10% FBS, L-Glutamine and HEPES. After seeding, cells were infected with PCV2B-Rm virus suspension (IF titer: 5-6 log 10 TCID50/ml) applying 0.01 or 0.05 MOI. The cells were cultured until reaching confluency (usually 3-5 days) without changing medium. Confluent cells were dissociated by trypsin and seeded in a T75 flask in fresh medium (30 ml/flask). After reaching confluency (usually 4-5 days) cells were split in T175 flasks in 50-60 ml medium. After reaching confluent stage the cells were frozen and then thawed. This cycle was repeated 3 times. After the third cycle the suspension was collected in sterile tubes and centrifuged at 3000 g for 10 minutes at 4° C. The supernatant was collected and the pellet is discarded. The virus suspension was stored at −20° C. or −70° C. Alternatively, a one step infection protocol could have been used. In this case, cells in T175 flasks (20,000/cm$^2$) could have been infected with PCV2B-Rm (MOI: 0.1), and incubated for 4-5 days. After reaching confluency, cells could have been frozen and thawed in a similar way as discussed above. By these methods 5-6 log 10 TCID$_{50}$/ml IF titers were reached.

Example 4

Inactivation of the Novel PCV2B-Rm Virus

These examples illustrate the inactivation of the produced/propagated PCV2B-Rm virus suspension by using ethylenimine.

Example 4.1

The synthesis of the inactivating agent ethylenimine (further referred as EI) was performed in 0.8% final concentration by the reaction of 0.2M 2-bromethylamin-hydrobromide and 0.4M sodium hydroxide at 37° C. for one hour.

Inactivation of the PCV2B-Rm virus suspension was done with the concentration of 0.05% (w/v) and 0.075% (w/v) at the temperature of 23° C. and 37° C. for 24 hours and 48 hours. The pH value of the EI stock solution was adjusted to 8.0-8.5 before being used for inactivation.

Inactivation was stopped by adding 50% (w/v) sodium-thiosulphate solution to the virus suspension in 1.5M excess then on the following day the pH was adjusted by adding glycin-HCl buffer to 7.2-7.4.

As prepared herein, the PCV2B-Rm virus was fully inactivated according to the appropriate inactivation control method irrespectively of the concentration, temperature and time applied during the inactivation.

Example 4.2

An alternative inactivation was performed by "in-situ" synthesis of the EI in the PCV2B-Rm virus suspension.

The first step of the inactivation was the synthesis of the EI directly in the virus suspension at 0.05% final concentration.

The virus suspension was pre-heated at 37° C. then 10% (w/v) 2-bromethylamin-hydrobromide solution was added to it. During the 6 hours synthesis the temperature of the virus suspension was kept at 37° C. and the pH was continuously adjusted by adding 1M sodium hydroxide to 7.8-8.2.

After finishing the synthesis the temperature of the virus suspension containing the EI at 0.05% (w/v) concentration was chilled at 23° C. then the inactivation was carried out for 24 hours. During the whole inactivation process the temperature was kept at 23° C.

Finally the inactivation was stopped by adding 50% (w/v) sodium-thiosulphate solution to the virus suspension in 1.5M excess and the pH was continuously adjusted between 7.5-7.8. The elimination of EI took place for 5 hours at 23° C.

As prepared herein, the PCV2B-Rm virus was fully inactivated according to the appropriate inactivation control method as well.

Example 5

Preparation of a PCV2B-Rm Virus Composition with Adjuvant (10% Oil)

The adjuvanted PCV2B-Rm virus composition was prepared as follow:

First Step:

A high shear rotor stator emulsifier was used to produce the formulations. To produce an emulsion, one volume of oily phase was emulsified at 25° C. with one volume of aqueous phase #1. The aqueous phase was added to the oily phase under agitation, 5000 rpm (rotation per minute) for 1 minute. The rotation speed was progressively increased with the augmentation of the volume to 10000 rpm during 1 minute. During this step the emulsion was a water-in-oil emulsion.

For the emulsion, phase composition was as follows:
Oily phase (200 ml):
Sorbitan monooleate: 1.8% v/v,
Sorbitan trioleate (20 OE): 10.2% v/v,
Light liquid paraffin oil: 88% v/v,
Aqueous phase #1 (200 ml):
20% (w/v) solution of sorbitan monooleate (20 OE): 11.25% v/v
Phosphate disodic and monopotassic 0.02M isotonic buffer (pH 7.2-7.6): 88.75% v/v Sorbitan monooleate and sorbitan trioleate (20 OE) were introduced in the oily phase.

A 20% (w/v) solution of sorbitan monooleate (20 OE) was prepared in the same buffer as the vaccine, for example, in phosphate disodic and monopotassic 0.02M isotonic buffer. When the agitation was stopped, then the emulsion changed to an oil-in-water emulsion. The emulsion was then placed in a cold chamber at 5° C. for at least 4 hours. At this stage, the emulsion was a pre-emulsion containing 50% of oily phase.

Second Step:

The aqueous phase #2 was prepared with 200 ml of phosphate disodic and monopotassic 0.02M isotonic buffer pH 7.2-7.6 with PCV2B-Rm. The pre-emulsion as prepared in the first step was cooled to about 5° C., diluted by adding half the volume of the aqueous phase #2 at the same temperature, and mixed by the rotation of a magnetic bar for 1 minute.

Example 6

Immunization of Swine (With Maternal Antibodies to PCV2)

Four-week-old female piglets were selected randomly from a PCV2 seropositive, conventional sow farm. Selected animals were transported to the experimental facilities and were acclimatized for 3 weeks until the first vaccination. During this period animals were weighed and blood samples were taken to assess the serological status of the piglets using an indirect immunofluorescence (IIF) assay (see below). Piglets were then divided into three groups, each containing 10 animals.

The first group of the piglets were vaccinated with the PCV2B-Rm virus vaccine with the adjuvant as prepared in Example 5 (Group A) on day 0 (7-week-old pigs). A first control group received the adjuvant as described in Example 5, only (Group B). A second control group received PBS only (Group C). A 2 ml volume was injected by intramuscular route. A second injection of vaccines or PBS was administered on day 21 (10-week-old pigs). On day 42, three weeks after the second vaccination, 7 pigs from each group were challenged by intranasal administration of 2 ml PCV2B-Rm virus suspension containing $10^3$ $TCID_{50}$ of PCV2-Rm virus/ml. The challenge virus was an early passage form of the PCV2B-Rm virus. After challenge, piglets were weighed on days 55 and 72. Rectal temperatures were recorded 3 days before the first vaccination (days −3, −2, −1, and on days 0, 1, 2, 3, 20, 21, 22, 23, 42, 43, 44, 45).

Blood samples were taken 7 days before the first vaccination (day −7), at the time of the second vaccination (day 21), at challenge (day 42) and on days 55, 64 and 72 for immunofluorescence serology. Sera were tested individually, diluted twofold, starting with 1:2 in PBS supplemented with 0.5% bovine serum albumin. PCV2 infected cells were fixed in an acetone/ethanol bath for 10 minutes at room temperature, and incubated for 1 hour at +37° C. with the serum dilutions. The secondary antibody was a 1:100 diluted anti-pig IgG labeled fluorescein isothiocyanate, for one hour at +37° C. Excess antibodies were removed by rinsing in PBS after each step, and the reaction was observed in a fluorescent microscope under ultraviolet light.

On days 42 and 55, 3-3 pigs, and on day 72 the last 4 pigs/groups were euthanized and subjected to necropsy. Mediastinal and mesenteric lymph nodes were collected for immunohistochemistry. The virus was detected and quantified by quantitative PCR, using the collected mesenterial lymph nodes.

Clinical Symptoms:

No significant difference was found in the mean body weights among the groups.

Immunofluorescence serology results of the vaccinated groups and the control (PBS) group as described in the Table 1:

TABLE 1

|  | A (adjuvant + PCV2B-Rm virus as prepared in Example 5) | B (adjuvant only) | C (PBS) |
|---|---|---|---|
| Day −7 | 64 | 181 | 148 |
| Day 21 (2nd vac.) | 338 | 237 | 444 |
| Day 42 (Challenge) | 1663 | 732 | 805 |
| Day 55 | 1722 | 4096 | 41285 |
| Day 64 | 2435 | 19484 | 8431 |
| Day 72 | 1448 | 11585 | 16384 |

After challenge, IF titers in group A remained basically at the same level as they had been before challenge. In the other group meaningful increase of the titers could be observed.

Immunohistochemistry:

Immunohistochemistry was performed based on the method described by Opriessnig et al. (2007; Opriessnig T, Meng X, Halbur P: 2007, Porcine circovirus type 2-associated disease: Update on current terminology, clinical manifestations, pathogenesis, diagnosis, and intervention strategies J Vet Diagn Invest 19: 591-615). 36A9 monoclonal antibody produced in mouse and an ENVISION anti-mouse HRP kit (Dako, Glostrup, Denmark) was used for the detection. Samples were scored according to the following criteria:

0=no antigen
1=antigen is detected in less than 10% of the follicles
2=antigen is detected in 10-50% of the follicles
3=antigen is detected in more than 50% of the follicles
std is an abbreviation for standard deviation Viral antigen was detected in the cytoplasm and nucleus of the macrophages.

TABLE 2

| Groups | Immunohistochemistry scores (mediastinal lymph nodes) (samples D42, 55, 72) | |
|---|---|---|
| | mean | std |
| A (adjuvanted PCV2B-Rm virus) | 0.25 | 0.43 |
| B (adjuvant only) | 1.33 | 0.58 |
| C (PBS) | 1.55 | 0.69 |

TABLE 3

| Groups | Immunohistochemistry scores (mesenterial lymph nodes) (samples D42, 55, 72) | |
|---|---|---|
| | mean | std |
| A (adjuvanted PCV2B-Rm virus) | 0.17 | 0.14 |
| B (adjuvant only) | 1.20 | 0.42 |
| C (PBS) | 1.36 | 0.63 |

The immunochemistry scores of the mediastinal (Table 2) and mesenterial (Table 3) lymph nodes in the control group were higher compared to the vaccinated groups. The lowest scores were found in group A. In general the scores of the mediastinal lymph nodes were higher compared to the mesenterial lymph nodes.

Real time PCR was performed according to the method described by Brunborg et al. (2004, Journal of Virological Methods 122: 171-178). PCV2 viral load was quantified using plasmid DNA containing PCV2 sequences. At the different sampling dates the copy numbers of PCV2 in the mesenterial lymph nodes were determined and are listed in the following Table 4:

TABLE 4

| Groups | Copy number | | | |
|---|---|---|---|---|
| | Day 42 (Challenge) | Day 55 | Day 72 | mean |
| A (adjuvanted PCV2B-Rm virus) | 7 | 38 | 2617 | 87 |
| B (adjuvant only) | 33756 | 132154 | 137168 | 84898 |
| C (PBS) | 42223 | 683163 | 101521 | 143069 |

The lowest copy numbers were found in group A.

Based on the results of IF serology, IHC and real time PCR the adjuvanted PCV2B-Rm vaccinated group were clearly protected after challenge with PCV2B virus.

The invention claimed is:

1. An isolated or inactivated porcine circovirus strain type 2 comprising SEQ ID NO: 1.

2. The porcine circovirus strain according to claim 1, wherein said porcine circovirus strain is an isolated porcine circovirus strain type 2 deposited at the Collection Nationale de Cultures de Microorganismes (CNCM) under accession No. CNCM I-4094.

3. The porcine circovirus strain according to claim 1, wherein said porcine circovirus strain is an isolated porcine circovirus strain type 2 comprising SEQ ID NO: 1.

4. The porcine circovirus strain according to claim 1, wherein said porcine circovirus strain is an inactivated porcine circovirus strain type 2 produced from the porcine circovirus strain type 2 deposited at the Collection Nationale de Cultures de Microorganisms (CNCM) under accession No. CNCM I-4094.

5. The porcine circovirus strain according to claim 1, wherein said porcine circovirus strain is an inactivated porcine circovirus strain type 2 comprising SEQ ID NO: 1.

6. A composition comprising a therapeutically effective amount of an inactivated porcine circovirus strain and a pharmaceutically acceptable vehicle, wherein said inactivated porcine circovirus strain type 2 comprises SEQ ID NO: 1.

7. The composition according to claim 6, wherein said inactivated porcine circovirus strain type 2 is produced from the porcine circovirus strain type 2 deposited at the Collection Nationale de Cultures de Microorganismes (CNCM) under accession No. CNCM I-4094.

* * * * *

UNITED STATES PATENT AND TRADEMARK OFFICE
CERTIFICATE OF CORRECTION

PATENT NO. : 8,703,468 B2  Page 1 of 1
APPLICATION NO. : 13/142090
DATED : April 22, 2014
INVENTOR(S) : Zoltan Penzes et al.

It is certified that error appears in the above-identified patent and that said Letters Patent is hereby corrected as shown below:

In the Specification

Column 3,
Line 63, "animal The" should read --animal. The--.

Column 5,
Line 31, "IFN-y," should read --IFN-γ,--.

Column 8,
Line 64, "the subject own" should read --the subject's own--.

In the Claims

Column 18,
Line 57, Claim 4, "Microorganisms" should read --Microorganismes--.

Signed and Sealed this
Seventeenth Day of February, 2015

Michelle K. Lee
*Deputy Director of the United States Patent and Trademark Office*

SEQUENCE LISTING

<160> NUMBER OF SEQ ID NOS: 3

<210> SEQ ID NO 1
<211> LENGTH: 1778
<212> TYPE: DNA
<213> ORGANISM: Porcine circovirus 2BRm

<400> SEQUENCE: 1

```
accagcgcac ttcggcagcg gcagcacctc ggcagcacct cggcagcacc tcagcagcaa      60
catgcccagc aagaagaatg gaagaagcgg accccaaccc cataaaaggt gggtgttcac     120
tctgaataat ccttccgaag acgagcgcaa gaaaatacgg gatcttccaa tatccctatt     180
tgattatttt attgttggcg aggagggtaa tgaggaagga cgaacacctc acctccaggg     240
gttcgctaat tttgtgaaga agcagacttt taataaagtg aagtggtatt tgggtgcccg     300
ctgccacatc gagaaagcga aaggaacaga tcagcagaat aaagaatact gcagtaaaga     360
aggcaactta ctgatggagt gtggagctcc tagatctcag ggacaacgga gtgacctgtc     420
tactgctgtg agtaccttgt tggagagcgg gagtctggtg accgttgcag agcagcaccc     480
tgtaacgttt gtcagaaatt tccgcgggct ggctgaactt ttgaaagtga gcgggaaaat     540
```

```
gcagaagcgt gattggaaga ctaatgtgca cgtcattgtg gggccacctg ggtgtggtaa    600
aagcaaatgg gctgctaatt ttgcagaccc ggaaaccaca tactggaaac cacctagaaa    660
caagtggtgg gatggttacc atggtgaaga agtggttgtt attgatgact tttatggctg    720
gctgccctgg gatgatctac tgagactgtg tgatagatat ccattgactg tagagactaa    780
aggtggaact gtaccttttt tggcccgcag tattctgatt accagcaatc agaccccgtt    840
ggaatggtac tcctcaactg ctgtcccagc tgtagaagct ctttatcgga ggattacttc    900
cttggtattt tggaagaatg ctacagaaca atccacggag gaagggggcc agttcgtcac    960
cctttccccc ccatgccctg aatttccata tgaaataaat tactgagtct tttttatcac   1020
ttcgtaatgg tttttattac tcattaaggg ttaagtgggg ggtctttaag attaaattct   1080
ctgaattgta catacatggt tacacggata ttgtattcct ggtcgtatat actgttttcg   1140
aacgcaatgc cgaggcctac gtggtctaca tttccagcag tttgtagtct cagccacagc   1200
tgatttcttt tgttgtttgg ttggaagtaa tcaatagtgg aatctaggac aggtttgggg   1260
gtaaagtagc gggagtggta ggagaagggc tgggttatgg tatggcggga ggagtagttt   1320
acataggggt cataggtgag ggctgtggcc tttgttacaa agttatcatc tagaataaca   1380
gcactggagc ccactcccct gtcaccctgg gtgatcgggg agcagggcca gaattcaacc   1440
ttaacctttc ttattctgta gtattcaaag ggcacagagc gggggtttga gccccctcct   1500
gggggaagaa agtcattaat attgaatctc atcatgtcca ccgcccagga gggcgttttg   1560
acagtggttc gcttgatagt atatccgaag gtgcgggaga ggcgggtgtt gaagatgcca   1620
tttttccttc tccagcggta acggtggcgg gggtggacga gccaggggcg gcggcggagg   1680
atctggccaa gatggctgcg ggggcggtgt cttcttctcc ggtaacgcct ccttggatac   1740
gtcatatctg aaaacgaaag aagtgcgctg taagtatt                           1778

<210> SEQ ID NO 2
<211> LENGTH: 53
<212> TYPE: DNA
<213> ORGANISM: Porcine circovirus 2BRm

<400> SEQUENCE: 2
accagcgcac ttcggcagcg gcagcacctc ggcagcacct cagcagcaac atg            53

<210> SEQ ID NO 3
<211> LENGTH: 11
<212> TYPE: DNA
<213> ORGANISM: Porcine circovirus 2BRm

<400> SEQUENCE: 3
cggcagcacc t                                                          11
```